(12) United States Patent
Jayakumar et al.

(10) Patent No.: US 8,039,260 B2
(45) Date of Patent: Oct. 18, 2011

(54) CHLOROPHYLLOUS TOTIPOTENT MAIZE CELL CULTURES

(75) Inventors: Pon Samuel Jayakumar, Fishers, IN (US); Nicole Linda Hopkins, Indianapolis, IN (US); Joseph F. Petolino, Zionsville, IN (US); Dayakar Reddy Pareddy, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 280 days.

(21) Appl. No.: 11/031,896

(22) Filed: Jan. 7, 2005

(65) Prior Publication Data

US 2005/0155119 A1    Jul. 14, 2005

Related U.S. Application Data

(60) Provisional application No. 60/535,579, filed on Jan. 8, 2004.

(51) Int. Cl.
*C12N 5/04* (2006.01)
(52) U.S. Cl. ..................... 435/412; 800/320.1
(58) Field of Classification Search .................. 800/293, 800/320.1, 298, 230; 435/420, 431, 410, 435/412
See application file for complete search history.

(56) References Cited

U.S. PATENT DOCUMENTS

| | | | |
|---|---|---|---|
| 4,326,034 A * | 4/1982 | Peel et al. ..................... | 435/420 |
| 4,535,060 A | 8/1985 | Comai | |
| 5,451,513 A | 9/1995 | Maliga et al. | |
| 5,693,507 A | 12/1997 | Daniell et al. | |
| 5,736,369 A | 4/1998 | Bowen et al. | |
| 5,886,244 A | 3/1999 | Tomes et al. | |
| 5,932,479 A | 8/1999 | Daniell et al. | |
| 6,004,782 A | 12/1999 | Daniell et al. | |
| 6,140,555 A | 10/2000 | Reichert et al. | |
| 6,235,529 B1 | 5/2001 | Lemaux et al. | |
| 6,486,384 B1 | 11/2002 | Zhang et al. | |
| 6,515,206 B1 | 2/2003 | Chaudhuri et al. | |
| 6,642,053 B1 | 11/2003 | Daniell et al. | |
| 6,680,426 B2 | 1/2004 | Daniell et al. | |
| 6,706,394 B2 | 3/2004 | Kuehnle et al. | |
| 2001/0031496 A1 | 10/2001 | Lemaux et al. | |
| 2003/0110687 A1 * | 6/2003 | Kozai et al. ............... | 47/58.1 LS |

FOREIGN PATENT DOCUMENTS

| | | | |
|---|---|---|---|
| WO | WO 97/32977 | | 9/1997 |
| WO | WO 99/10513 | * | 3/1999 |

OTHER PUBLICATIONS

Aftab et al. Plant regeneration from embryogenic cell suspensions and protoplasts in sugarcane (*Saccharum* spp. hybrid cv. CoL-54). Plant Cell, Tissue and Organ Culture. 44: 71-78, 1996.*
Fitch et al. Comparison of 2,4-D and picloram for selection of long-term totipotent green callus culture of sugarcane. Plant Cell, Tissue and Organ Culture. 20: 157-163, 1990.*

Goldstein et al. Photosynthetic characterization of photoautotropic cells cultured in a minimal mediium. Plant Physiol. (1990) 94, 1641-1646.*
Ishimaru et al. Induction of photomixotrophic callus from the germ disk of mature cultivated rice seed and its use in studies of photosynthetic capacity. International Journal of Experimental Botany, 59 (1/2): 197-200, XII, 1996.*
Norman et al. Uptake and metabolism of clomazone in tolerant-soybean and susceptible-cotton photomixotrophic cell suspension cultures. Plant Physiol. (1990) 92, 777-784.*
Swedlund et al. Sorbitol as the primary carbon source for the growth of embryogenic callus of maize. Plant Physiol. (1993) 103: 1339-1346.*
Solis et al. The Biogenesis of Chloroplast in Tissue Cultures of a C3 and a C4 Plant. Plant Cell Physiol. 30(5): 609-616 (1989).*
Xiao et al. Photoautotrophic Growth of Sugarcane Plantlets In Vitro as Affected by Photosynthetic Photon Flux and Vessel Air Exchanges. In Vitro Cell. Dev. Biol.—Plant 39: 186-192 (2003).*
Murthy et al. Thidiazuron: A potent regulator of in vitro plant morphogenesis. In Vitro Cell. Dev. Biol.—Plant 34:267-275, 1998.*
Aguado-Santacruz, G.A. et al. "Establishment, characterization and plant regeneration from highly chlorophyllous embryonic cell cultures of blue grama grass, *Bouteloua gracilis* (H.B.K.) Lag, ex Steud." *Plant Cell Reports*, 2001, pp. 131-136, vol. 20.
Ali, G. et al. "Morphogenic and biochemical responses of *Bacopa monniera* cultures to zinc toxicity" *Plant Science*, 1999, pp. 187-193, vol. 143.
Armstrong, C.L. and Green, C.E. "Establishment and maintenance of friable, embryogenic maize callus and the involvement of L-proline" *Planta*, 1985, pp. 207-214, vol. 164.
Arnon, D.I. "Copper enzymes in isolated chloroplasts, polyphenol 1oxidase in *Beta vulgaris*." *Plant Physiology*, 1949, pp. 1-15, vol. 24.
Boynton, J.E. et al. "Chloroplast transformation in *Chlamydomonas* with high velocity microprojectiles." *Science*, 1988, pp. 1534-1538, vol. 240.
Carrer, H. et al. "Kanamycin resistance as a selectable marker for plastid transformation in tobacco." *Mol Gen Genet*., 1993, pp. 49-56, vol. 24(1-2).
Cho, M.J. et al. "High frequency transformation of oat via microprojectile bombardment of seed-derived highly regenerative cultures." *Plant Science*, 1999, pp. 9-17, vol. 148.
Cho, M.J. et al. "Transformation of recalcitrant barley cultivars through improvement of regenerability and decreased albinism." *Plant Science*, 1998, pp. 229-244, vol. 138.
Cho, M.J. et al. "Production of transgenic tall fescue and red fescue plants by particle bombardment of mature seed-derived highly regenerative tissues" *Plant Cell Reports*, 2000, pp. 1084-1089, vol. 19.

(Continued)

*Primary Examiner* — June Hwu
(74) *Attorney, Agent, or Firm* — James Daly, IV; Kenneth Ludwig

(57) ABSTRACT

The subject invention provides totipotent, chlorophyllous, cell cultures of maize. In addition, the methods of producing such cultures are applicable to other related species, including cereals such as rice, oats, barley, and heat. The subject cultures are valuable for herbicide studies, studies for enhancing photosynthesis, and genetic manipulation, such as plastid transformation. The methods of the subject invention are capable of providing high percentages of totipotent cells. These cells are capable of sustained cell division and are competent for regeneration over long periods; they provide high-quality target tissue for nuclear and organelle transformation. The invention also describes methods for the introduction of heterologous DNA into the chloroplast genome. The present invention also provides methods, vectors, and gene constructs for enhancing expression of a recombinant nucleic acid sequence in transgenic plants and plant tissues.

1 Claim, 3 Drawing Sheets

OTHER PUBLICATIONS

Cho, M.J. et al. "Transformed T$_0$ orchardgrass (*Dactylis glomerata* L.) plants produced from highly regenerative tissues derived from mature seeds." *Plant Cell Reports*, 2001, pp. 318-324, vol. 20.

D'Halluin, K. et al. "Transgenic maize plants by tissue electroporation." *The Plant Cell*, 1992, pp. 1495-1505, vol. 4.

Dufourmantel, N. et al. "Generation of fertile transplastomic soybean." *Plant Molecular Biology*, 2004, pp. 479-489, vol. 55(4).

Fromm, H. et al. "The molecular basis for rRNA-dependent spectinomycin resistance in *Nicotiana* chloroplasts." *EMBO Journal*, 1987, pp. 3233-3237, vol. 6(11).

Gorodn-Kamm, W.J. et al. "Transformation of maize cells and regeneration of fertile transgenic plants." *The Plant Cell*, 1990, pp. 603-618, vol. 2.

Hiei, Y. et al. "Transformation of rice mediated by *Agrobacterium tumefaciens*." *Plant Mol Biol.*, 1997, pp. 205-218, vol. 35.

Kavanagh, T.A. et al. "Homeologous plastid DNA transformation in tobacco is mediated by multiple recombination events." *Genetics*, 1999, pp. 1111-1122, vol. 152.

Kumar, S. et al. "Plastid-expressed *Betaine Aldehyde Dehydrogenase* gene in carrot cultured cells, roots, and leaves confers enhanced salt tolerance." *Plant Physiology*, 2004, pp. 2843-2854, vol. 136.

Laursen, C.M. et al. "Production of fertile transgenic maize by electroporation of suspension culture cells" *Plant Molecular Biology*, 1994, pp. 51-61; vol. 24.

Le, B.V. et al. "Rapid regeneration of whole plants in large crabgrass (*Digitaria sanguinalis* L) using thin cell-layer culture." *Plant Cell Reports*, 1998, pp. 166-172, vol. 18.

Lössl, A. et al. "Polyester synthesis in transplastomic tobacco (*Nicotiana tabacum* L.): significant contents of polyhydroxybutyrate are associated with growth reduction." *Plant Cell Rep*, 2003, pp. 891-899, vol. 21.

Lowe, K. et al. "Germline transformation of maize following manipulation of chimeric shoot meristems." *Nature Biotechnology*, 1995, pp. 677-682, vol. 13(7).

McBride, K et al. "Controlled expression of plastid transgenes in plants based on a nuclear DNA-encoded and plastid-targeted T7 RNA polymerase." *Proc. Natl. Acad. Sci.*, 1994, pp. 7301-7305, vol. 91.

O'Neill, C. et al. "Chloroplast transformation in plants: polyethylene glycol (PEG) treatment of protoplasts is an alternative to blolistic delivery systems." *Plant Journal*, 1993, pp. 729-738, vol. 3(5).

Rhodes, C.A. et al. "Genetically transformed maize plants from protoplasts." *Science*, 1988, pp. 204-207, vol. 240(4849).

Ruf, S. et al. "Stable genetic transformation of tomato plastids and expression of a foreign protein in fruit." *Nature Biotechnology*, 2001, pp. 870-875, vol. 19(9).

Sidorov, V.A. et al. "Stable chloroplast transformation in potato: use of green fluorescent protein as a plastid marker." *The Plant Journal*, 1999, pp. 209-216, vol. 19(2).

Sikdar. S.R. et al. "Plastid transformation in *Arabidopsis thaliana*." *Plant Cell Reports*, 1998, pp. 20-24, vol. 18.

Svab, Z. et al. "High-frequency plastid transformation in tobacco by selection for a chimeric *aadA* gene." *Proc. Natl. Acad. Sci.*, 1993, pp. 913-917, vol. 90.

Svab, Z. et al. "Stable transformation of plastids in higher plants." *Proc. Natl. Acad. Sci.*, 1990, pp. 8526-8530, vol. 19(9).

Welter, M.E. et al. "Morphotypes of friable embryogenic maize callus" *Plant Cell Reports*, 1995, pp. 725-729, vol. 14.

Zhang, S. et al. "Genetic Transformation of commercial cultivars of oat (*Avena sativa* L) and barley (*Hordeum vulgare* L.) using shoot meristematic cultures derived from germinated seedlings." *Plant Cell Reports*, 1990, pp. 959-966, vol. 18.

Zoubenko, O.V. et al. "Efficient targeting of foreign genes into the tobacco plastid genome." *Nucleic Acids Research*, 1994, pp. 3819-3824. vol. 22(19).

* cited by examiner

CHLOROPHYLLOUS TOTIPOTENT MAIZE CELL CULTURES

CROSS-REFERENCE TO RELATED APPLICATION

This application claims priority to provisional application Ser. No. 60/535,579, filed Jan. 8, 2004.

FIELD OF THE INVENTION

The present invention relates to plant biology and the application of genetic engineering techniques to plants. More particularly, the present invention provides compositions and methods involving chlorophyllous totipotent cell cultures useful for controlled manipulations of plants at the cellular level.

BACKGROUND OF THE INVENTION

Recombinant DNA technology and genetic engineering have made it possible to introduce desired DNA sequences into plant cells to allow for the expression of proteins of interest. The relative ease of obtaining commercially viable transformation events in important crops, however, remains a challenge.

Transformation of plant cells and tissues with foreign DNA can be achieved in a number of ways known to the art. For example, (a) particle bombardment of cultured cells (Gordon-Kamm et al., 1990, and U.S. Pat. No. 5,886,244), immature embryos (Koziel et al., 1993), meristems (Lowe et al., 1995); (b) electroporation of immature embryos (D'Halluin et al., 1992), cultured cells (Laursen et al., 1994); (c) electroporation and/or polyethylene glycol treatment of protoplasts (Rhodes et al., 1989; Omirulleh et al., 1993), and (d) co-cultivation with *Agrobacterium tumefaciens* (Ishida et al., 1996; Hiei et. al., 1997; Zhao et al., 1998). See also U.S. Pat. No. 6,706,394, which relates to the use of magnetizable microparticles and magnetic fields for transformation.

Cho et al. (*Plant Science* 138 [1998] 229-244) relates to a system for transformation of barley. Cho et al. (*Plant Science* 148 [1999] 9-17) relates to a system for transformation of oats. Cho et al. (Plant Cell Reports [2000] 19:1084-1089) relates to the production of transgenic fescue by particle bombardment. Cho et al. (Plant Cell Reports [2001] 20: 318-324) relates to transformed orchardgrass. U.S. 20010031496 A1 and U.S. Pat. No. 6,235,529 relate to plant transformation and regeneration. U.S. Pat. Nos. 5,736,369 and 6,486,384 relate to the transformation of cereals. U.S. Pat. No. 6,140,555 relates to maize transformation. Zhang et al. (Plant Cell Reports [1999] 18: 959-966) relates to an oat transformation system that uses high concentrations of mannitol and sorbitol (0.2M) as osmotic treatments prior to particle bombardment. This is done to partially desiccate the cells so that they do not burst upon impact by the particles.

Plant cells can be grown in isolation from intact plants in tissue culture systems. Plant tissue cultures can be initiated from almost any part of a plant. Pieces of plant tissue will slowly divide and grow into a colorless mass of cells if they are kept in special in vitro culture conditions. The cells have the characteristics of callus cells, rather than other plant cell types. Callus cells appear on cut surfaces when a plant is wounded; these cells gradually cover and seal the damaged area.

Tissue culture cells generally lack the distinctive features of most plant cells. They have a small vacuole, and lack chloroplasts and photosynthetic pathways; structural or chemical features that distinguish many cell types within the intact plant are absent. They are most similar to the undifferentiated cells found in meristematic regions; the cells become fated to develop into each cell type as the plant grows. Tissue cultured cells can also be induced to re-differentiate into whole plants by alterations to the growth media.

Totipotency is the ability of undifferentiated plant cells to develop, in vitro, into whole plants or plant organs, when given the optimum in vitro culture conditions. Totipotent cells that undergo rapid division are generally regarded as highly suitable targets for introduction of DNA as a first step in the generation of transgenic plants. In corn, one prolific source of such cells is the so-called Type II callus (Armstrong and Green, 1985).

In maize, totipotent cell cultures typically proliferate in vitro as clusters of non-green cells and only synthesize chlorophyll in mature chloroplasts upon shoot differentiation during plant regeneration. However, green or chlorophyllous cultures organize plastome structures in the presence of light and develop chloroplasts. The cell cultures of photoautotrophic or photomixotrophic cells have functional chloroplast in a sugar-free or minimal medium, respectively. Such cultures are common in dicots, and several plants such as soybean, tobacco, Chenopodium, Datura, and cotton can be used for making such cultures routinely. However, such cultures are rare or nonexistent for most or all monocots, with an exception of blue grama grass (green embryogenic suspension cells) (Aguado-Santacruz et al. 2001: *Plant Cell Rep* 20: 131-136). There are few, if any, other reports of monocots where some green callus/tissue development was achieved. Any such attempts were typically aimed at improving regeneration or improved recovery of transgenic plants.

The plastids of higher plants are an attractive target for genetic engineering. Chloroplast (a type of plastid) transformation has been achieved and is advantageous. See e.g. U.S. Pat. Nos. 5,932,479; 6,004,782; and 6,642,053. See also U.S. Pat. Nos. 5,693,507 and 6,680,426. Advantages of transformation of the chloroplast genome include:

1) potential environmental safety because transformed chloroplasts are only maternally inherited and thus are not transmitted by pollen out crossing to other plants;
2) the possibility of achieving high copy number of foreign genes; and
3) eduction in plant energy costs because importation of proteins into chloroplasts, which is highly energy dependent, is reduced.

Plant plastids (chloroplasts, amyloplasts, elaioplasts, etioplasts, chromoplasts, etc.) are the major biosynthetic centers that, in addition to photosynthesis, are responsible for producing many industrially important compounds such as amino acids, complex carbohydrates, fatty acids, and pigments. Plastids are derived from a common precursor known as a proplastid; thus, the plastids in a given plant species all have the same genetic content.

Plastids of most plants are maternally inherited. Consequently, unlike heterologous genes expressed in the nucleus, heterologous genes expressed in plastids are not disseminated in pollen. Therefore, a trait introduced into a plant plastid will not be transmitted to wild-type relatives. This offers an advantage for genetic engineering of plants for tolerance or resistance to natural or chemical conditions, such as herbicide tolerance, as these traits will not be transmitted to wild-type relatives.

The plastid genome (plastome) of higher plants is a circular double-stranded DNA molecule of 120-160 kb which may be present in 1,900-50,000 copies per leaf cell (Palmer, 1991). In general, plant cells contain 500-10,000 copies of a small 120-160 kilobase circular genome, each molecule of which has a large (approximately 25 kb) inverted repeat. Thus, it is possible to engineer plant cells to contain up to 20,000 copies of a particular gene of interest; this can potentially result in very high levels of foreign gene expression.

Stable transformation of the tobacco plastome has been achieved through the following steps: (i) introduction of transforming DNA, encoding antibiotic resistance, by the biolistic process (Svab et al. 1990; Svab and Maliga 1993) or PEG treatment (O'Neill et al., 1993), (ii) integration of the transforming DNA by two homologous recombination events and (iii) selective elimination of the wild-type genome copies during repeated cell divisions on a selective medium. Spectinomycin resistance has been used as a selective marker encoded either in mutant plastid 16S ribosomal RNA genes (Svab et al. 1990; Staub and Maliga 1992), or conferred by the expression of an engineered bacterial aadA gene (Svab and Maliga 1993). Vectors that utilize aminoglycoside adenyltransferase (aadA) as a selectable marker gene, and target the insertion of chimeric genes into the repeated region of tobacco plastome, are available (Zoubenko et al., 1994). Selection of plastid transformants by kanamycin resistance, based on the expression of neomycin phosphotransferase, is more difficult but also feasible (Carrer et al., 1993).

Until recently, successful plastid transformation techniques for higher plants have been limited to model crop plants such as tobacco (U.S. Pat. No. 5,451,513; Svab et al. (1990), *Proc. Natl. Acad. Sci. USA* 87: 8526-8530 and Svab et al. (1993), *Proc. Natl. Acad. Sci. USA* 90: 913-197) and *Arabidopsis* (Sikdar, et al. (1998) *Plant Cell Reports* 18: 20-24). A review of plastid transformation of flowering plants is provided by Maliga (1993) Trends in Biotech. 11: 101-107.

Furthermore, the methods described for *Arabidopsis* plants, produce infertile regenerates. PCT Publication WO 97/32977 also describes methods for the plastid transformation of *Arabidopsis* and provides prophetic examples of plastid transformation of *Brassica* plastids. However, transplastomic *Brassica* plants were not produced using the methods described therein. U.S. Pat. No. 6,515,206 relates to plastid transformation of *Brassica*.

Plastomic transformation was extended to potatoes and tomatoes (see e.g. Sidorov et al., *The Plant Journal*, vol. 19, iss. 2, page 209 (July 1999); and Ruf et al., *Nature Biotechnology*, vol. 9, no. 9, pp. 870-875 (September 2001); respectively). However, these plants are closely related to tobacco, and it is possible to work the tobacco protocol to produce transplastomic tomato and potato. Thus, one would not have expected to apply the tobacco technology beyond the tobacco family (Nicotinaceae) to crop plants.

More recently, three more plants have been shown to be susceptible to plastomic transformation: cotton, carrots, and soybeans (see e.g. Kumar and Daniell, *Plant Molecular Biology*, "Manipulation of gene expression facilitates cotton plastid transformation of cotton by somatic embryogenesis and maternal inheritance of transgenes" in press (2004); Kumar and Daniell, *Plant Physiology*, "Plastid expressed betaine aldehyde dehydrogenase gene in carrot cultured cells, roots and leaves confers enhanced salt tolerance," in press (2004); and Nathalie Dufourmantel, Bernard Pelissier, Frederic Garcon, Gilles Peltier, Jean-Marc Ferullo, Ghislaine Tissot, "Generation of fertile transplastomic soybean," *Plant Molecular Biology*, Volume 55, Issue 4, July 2004, Pages 479-489). The use of tissues other than leaf explants as target material has been demonstrated in all three of these plants, where the target material was embryos or embryogenic callus. However, there appears to be limitations in the selectable markers that could be successfully used to achieve plastomic transformation. This is currently limited to only Spectinomycin, aphA6/npt (neomycin class antibiotic), and EPSPS (5-enolpyruvylshikimate-3-phosphate synthase) marker (including the other ones glyphosate oxido -reductase (GOX) and the aroA gene see U.S. Pat. No. 4,535,060). Biolistics is the most preferred DNA delivery method that is used to enable this technology in these system. PEG mediated delivery has been also reported, but not widely used to transform plastids.

With possibly one exception of blue grama grass (Aguado-Santacruz et al. 2001: *Plant Cell Rep* 20: 131-136), no other monocots (including any cereal cultures) are reported to be chlorophyllous, photoautotropic, and/or photomixotropic. The methods of Aguado-Santacruz et al. were unsuccessfully applied to maize. See Example 10, below.

For corn and cereals, as well as dicots, a chlorophyllous photoautotropic suspension system that remains embryogenic and could regenerate into plants would be ideal for photosynthetic, herbicidal, and plastid genetic manipulation studies. However, such systems have not heretofore been known in the art.

SUMMARY OF THE INVENTION

Disclosed herein, for the first time, are totipotent, chlorophyllous cell cultures of maize. In addition, the methods of producing such cultures are applicable to other related species, including cereals such as rice, barley, and wheat.

The subject cultures are valuable for herbicide studies and genetic manipulation, such as plastid transformation. The methods of the subject invention are capable of providing high percentages of totipotent cells. These cells are capable of sustained cell division and are competent for regeneration (over long periods); they provide high-quality target tissue for transformation.

The invention also describes methods for the introduction of heterologous DNA into the chloroplast genome. The present invention also provides methods, vectors, and gene constructs for enhancing expression of a recombinant nucleic acid sequence in transgenic plants and plant tissues.

DETAILED DESCRIPTION

Figure 1:
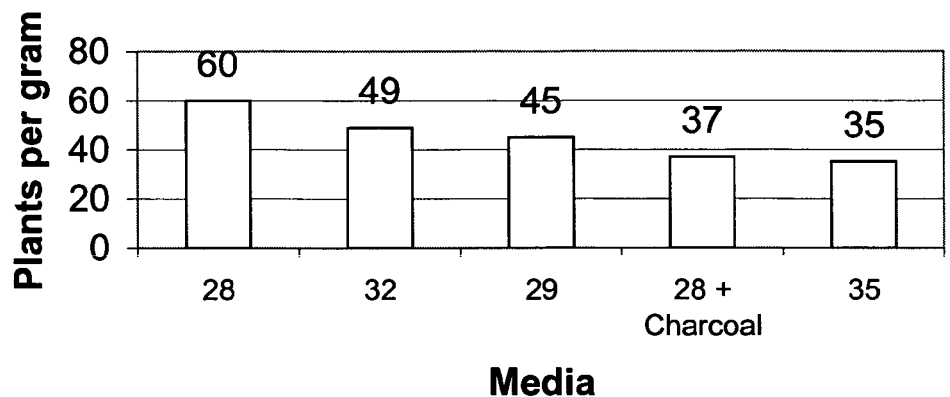
FIG. 1 shows that the regeneration frequency is quite high in the maize regeneration medium.

The subject invention provides totipotent, chlorophyllous cell cultures of maize. In addition, the subject invention provides methods of producing such cultures, and these methods are applicable to other related species, including cereals such as rice and wheat.

The methods of the subject invention are capable of providing high percentages of totipotent cells. These cells are capable of sustained cell division and are competent for regeneration (over long periods); they provide high-quality target tissue for transformation.

The invention also describes methods for the introduction of heterologous DNA into the chloroplast genome. The present invention also provides methods, vectors, and gene constructs for enhancing expression of a recombinant nucleic acid sequence in transgenic plants and plant tissues.

The subject cultures are valuable for herbicide studies and genetic manipulation, such as plastid transformation. Plastid transformation, in which genes are inserted by homologous recombination into some or all of the several thousand copies of the circular plastid genome present in each plant cell, takes advantage of the enormous copy number advantage over nuclear-expressed genes to permit expression levels that may exceed 10% of the total soluble plant protein. In addition, plastid transformation is desirable because in most plants plastid-encoded traits are not pollen transmissible; hence, fear of inadvertent transgene escape to wild relatives of transgenic plants is avoided. Plastid transformation technology is extensively described in U.S. Pat. Nos. 5,451,513, 5,545,817, 5,545,818 and 5,576,198; in PCT application Nos. WO 95/16783 and WO 97/32977; and in McBride et al., *Proc. Natl. Acad. Sci. USA* 91: 7301-7305 (1994). Plastid transformation via biolistics was achieved initially in the unicellular green alga *Chlamydomonas reinhardtii* (Boynton et al. (1988) *Science* 240: 1534-1537). This approach, using selection for cis-acting antibiotic resistance loci (spectinomycin/streptomycin resistance) or complementation of non-photosynthetic mutant phenotypes, was soon extended to *Nicotiana tabacum* (Svab et al. (1990) *Proc. Natl. Acad. Sci. USA.* 87: 8526-8530).

As mentioned above in the Background section, chlorophyllous maize cell cultures were not previously known in the art. Many selectable markers for dicot transformation yield successful transformants that lack green color when transformation has occurred. Thus, it is clear that those markers would be of no value in tissue cultures that are not green. A "green" maize tissue culture would be particularly advantageous, and would greatly increase the range of options for selectable markers. Heretofore, the art turned to finding new markers for maize transformation that did not depend on a green culture as a point of reference. The subject invention relates to quite an undertaking, in that rather than trying to find a new marker, the subject invention actually provides "green" tissue cultures (of maize cells, rice cells, and the like, for example) that produce chloroplasts. Not only are these tissue cultures extremely valuable for various transgenic assays, the subject invention provides methods that can be used to produce other monocot tissue cell cultures that were not heretofore achievable.

Quite apparently, the methods used to produce such cultures are unique. For example, the materials and methods used to obtain the blue grama grass cultures of Aguado-Santacruz et al. (the only known green monocot tissue culture), were used unsuccessfully in an attempt to produce green maize tissue cultures.

When "media" is referred to generically below, unless otherwise indicated, this relates to the "induction" media of the subject invention. This is used to grow an existing culture in conditions that allow the green color (i.e., the production of chloroplasts) to develop. The existing cultures are grown on regular, pre-induction media. The subject invention, in part, relates to the induction media and the use thereof to achieve surprising benefits (heretofore non-achievable cultures).

In preferred embodiments, a maize cell culture is grown, in the presence of light, on induction media substantially lacking sucrose while comprising zinc, copper, and a growth hormone. Thus, essential elements of the media of the subject invention are near-starvation conditions, the metals, and the hormone, and the cultures on this media are grown in the presence of light (preferably bright, full-spectrum light (such as that described in the Examples below).

Growth Hormone

In preferred embodiments, the growth hormone used in the induction media of the subject invention is thidiazuron (TDZ). Some alternatives might be used, such as diuron. Preferred concentrations can vary but can preferably be used in the range of 10-100 μM.

Thidiazuron (TDZ) is a substituted cytokinin-like phenylurea. It is a non-purine compound unlike many of the known cytokinins that are commonly used in monocot tissue culture. It has been successfully used to develop thin layer cell cultures in rice (Bui et al., 1998). This compound is very potent and is capable of eliciting plant responses in 1 fM to 50 mM concentration. This wide range can be used as the active range for the induction of the green suspensions of the subject invention.

Carbon Source

In preferred embodiments, the media uses sorbitol as the carbon source. The media is substantially or completely free of sucrose. Mannose, manitol, and maltose can be used as alternatives to sorbitol for some applications.

Sorbitol is a carbon source and can be used according to the subject invention at an approximate concentration of 30 g/l in the medium, in some embodiments. It is possible that the concentration of this compound could be as high as about 60 g/L in the medium, especially when the suspension is desiccated (in the preparatory steps towards delivering the DNA).

Preferably, the concentration of sorbitol is approximately half of that typically used for sucrose (typically approximately 30 g/L or 3%). Thus, preferred concentrations of sorbitol can be approximately 3-16 g/L. The sorbitol concentration is not high enough to significantly alter the osmotic properties of the media. Very high concentrations of sorbitol were previously used for bombardment pretreatment (not for inducing greening), but those concentrations are much higher than those of the subject invention. In those prior uses, very high concentrations of sorbitol were used to dry cells that would be subject to particle bombardment. That is done because plump cells can be lysed upon particle bombardment.

In this medium (for inducing greening of suspension cells), sorbitol is substituted for sucrose in order to provide an environment for the proplastid/amyloplast in the suspension cells to differentiate chloroplasts. This makes the suspension cells fully or partially autonomous for the carbon source. This substitution is essential, as sucrose or glucose in the medium inhibits chloroplast biogenesis.

Metals

In addition to a growth hormone (TDZ) and sorbitol as the carbon source, the metals (copper and zinc) are also important to have for the development of the green suspensions in maize. (The elimination of any one of these components leads to undesirable results leading to the necrosis of culture.) Heavy metals such as manganese (Mn), iron (Fe), copper (Cu), zinc (Zn), molybdenum (Mo) and nickel (Ni) are micronutrients necessary to support life in biological systems (Welch, 1995). Among these, zinc is necessary for the production of chlorophyll and carbohydrates, and aids in the creation of plant growth substances, enzyme systems, and metabolic reactions. Copper is necessary for chlorophyll formation and also acts as a catalyst for other plant reactions.

The metals of the subject invention are used at relatively very high concentrations. Without being bound by a specific theory of a mechanism of action, zinc and copper are believed to quench superoxide dismutase (SOD).

Zinc (Zn) concentrations as low as 1 μm have been reported to provide adequate physiological requirements of zinc for plant mineral nutrition (Taiz & Zeiger, 1998). Nanda Kumar et al. (1995) reported that 100 mg Zn/l (corresponding to 1529 μm) were not phytotoxic to *Brassica juncea* when added to soil mixtures. Ralph and Burchett (1998) observed an increase in total chlorophyll concentrations after treatment with 10 mg/l of Zn (that is 153 μm) in *Halophila ovalis*. Gayoor et al. (1999) observed beneficial effect on photosynthesis and translocation of photosynthates in *B. monniera* between 100 μm and 600 μm of ZnSO4. Concentrations of this compound in the subject cultures can exceed 600 μm.

Copper (Cu) is involved in chlorophyll synthesis, and nearly 70% of all copper in the leaves is found in the chloroplasts. Copper is also a constituent of plastocyanin—a chloroplast protein that is part of the photosynthetic electron transport system. Copper is also a constituent of several oxidases (enzymes that catalyze oxidation-reduction reactions). It may play a role in elemental nitrogen fixation in legumes and in the production of vitamin A. However, in high concentrations, Cu is toxic; plant species tolerate concentrations to certain level, termed the "critical level" (Korzeniowska and Stanlslawska-Glublak, 2003). USEPA [1992] reported that 40-mg kg$^{-1}$ Cu in maize shoots did not decrease top growth; this tissue concentration was identified as the "No Observable Adverse Effect Level." According to MacNicol and Backett [1985], and Mocquot et al. [1996], the critical level of Cu in maize shoots was 21 mg kg$^{-1}$. Borkert et al. [1998] confirmed that 20 mg kg$^{-1}$ was the critical Cu toxicity level for maize leaves and also for rice. According to the subject invention, a preferred concentration used for the induction of the green suspension is 5 uM; a higher level, up to about 100 uM, could be used in the cultures.

Other Aspects of the Subject Invention

While suspensions are exemplified, plated cultures can also be used according to the subject invention.

The subject invention is not limited to maize cells, but can also be extended to other cereals, such as wheat, oats, barley, millet, sorghum, and rice. See, e.g., Example 11.

In preferred embodiments, the subject invention is used to express large titers of recombinant proteins of interest. Proteins of interest can include antigens, antibodies, *Bacillus thuringiensis* pesticidal proteins, and proteins, polypeptides, and peptides having biological activities, such as pharmaceutical activities, antimicrobial activities, and the like.

Cells of the subject invention can be grown into whole plants. Thus, the subject invention includes plants regenerated from cell cultures of the subject invention. Regeneration techniques, some of which are discussed above in the Background section, are known in the art and can be adapted for use according to these aspects of the subject invention. In addition, cells can be used in bioreactors to produce the protein of interest.

The subject invention includes the use of green maize cell cultures for plastid transformation. Various transformation techniques, some of which are described in the Background section above and elsewhere herein, are known in the art and can be adapted for use according to these aspects of the subject invention. Practically any transformation technique can be used to introduce the heterologous gene into the cells of the subject invention, but some techniques are preferred. One preferred method is micro aerosol beaming, as discussed in Example 13. See also U.S. Pat. No. 5,240,842. "WHISKERS" or microfiber transformation (see e.g. U.S. Pat. No. 5,302,523) is a preferred method, as is microparticle bombardment, electroporation, PEG, and *Agrobacterium*, which are discussed elsewhere herein in more detail.

The following definitions might be useful for understanding various aspects of the subject invention:

Callus—Proliferating mass of cells or tissue in vitro.

Type I—A compact, slow growing, heteromorphic callus (embryogenic/organogenic) which retains meristematic activity in regions of organized tissue.

Type II—A friable, fast growing embryogenic callus composed of aggregates of small isodiametric cells with dense cytoplasm. Often contains small embryoids attached to the underlying callus by a suspensor.

Embryogenic Callus—A type of callus capable of differentiating into somatic embryos.

Germinal Cells (Gametes)—Cells of an organism which are capable of transferring their genetic information to the next generation.

Genotype—The genetic complement of an organism.

Heterologous DNA—DNA from a source different than that of the recipient cell.

Homologous DNA—DNA from the same source as that of the recipient cell.

Hybrid—Progeny resulting from a cross between parental lines.

Inbred Lines—organisms that are genetically homogeneous (homozygous) resulting from many generations of self crossing.

In vitro—In the laboratory.

In vivo—In the living organism.

Monocot—Plants having a single cotyledon (the first leaf of the embryo of seed plants); examples include cereals such as maize, rice, wheat, oats and barley.

Non-Embryogenic Callus—A type of callus composed of undifferentiated, often highly vacuolated cells which are unable to be induced to form embryos.

Phenotype—Traits exhibited by an organism resulting from the interaction of genotype and environment.

Protoplast—Plant cells exclusive of the cell walls.

Somatic Cells—Body cells of an organism, exclusive of germinal cells.

Totipotency—the ability of undifferentiated plant cells to develop, in vitro, into whole plants or plant organs, when given the correct conditions.

Transformation—Acquisition of new genetic coding sequences by the incorporation of added (exogenous) DNA.

Transgenic—Organisms (plants or animals) into which new DNA sequences are integrated.

Culture medium, as referred to herein, is plant tissue culture medium that contains plant growth regulators in combination with macronutrients and micronutrients that are essential for the sustained growth of the tissue in vitro. The medium formulated for inducing the greening of suspension cells, described herein, is a minimal medium. The suspension cells are used according to the subject invention as target or recipient cells for plastid transformation via Whiskers™ (described below), biolistics (Assem et al., 2002), PEG (Goulds et al., 1993) mediated DNA delivery, and the like.

Having thus described in detail preferred embodiments of the present invention, it is to be understood that the various described embodiments are merely exemplary of the present invention and that many apparent variations thereof are possible without departing from the spirit or scope thereof. Accordingly, one skilled in the art will readily recognize that the present invention is not limited to the specific embodiments described herein.

The description provided in the following examples relates to the preferred method using the available strategy from the published protocols for constructing DNA vectors and for applying the target tissue of the present invention successfully toward the goal of achieving maize/cereal plastid transformation. Any molecular cloning and recombinant DNA techniques needed would be carried out by standard methods (Sambrook et al., 1995)

All patents, patent applications, provisional applications, and publications referred to or cited herein are incorporated by reference in their entirety to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

EXAMPLES

Example 1

Establishment of Starter Suspension (Non-Green) Cells of Hi-II Maize Genotype for the Initiation of Green Suspension Cells In maize, the embryogenic suspension cultures are typically produced from callus cultures of the genotype "Hi-II" (Armstrong et al. 1991). Such callus cultures are initiated from 0.8-2.0 mm zygotic embryos isolated from ears 9-13 days post-pollination following surface sterilization with 70% ethanol for 2 minutes and 20% commercial bleach (1% sodium hypochlorite) for 30 minutes. Callus initiation medium consists of N6 basal salts and vitamins (Chu et al. 1975), 20 g/L sucrose, 25 mM L-proline, 100 mg/L casein hydrolysate, 10 mg/L $AgNO_3$ and 1.0 mg/L 2,4-diclorophenoxy acetic acid (2,4-D) adjusted to pH 5.8 and solidified with 2.0 g/L Gelrite® (Aceto Corp., Lake Success, N.Y.). After 8 weeks of 2-week subcultures, the $AgNO_3$ is omitted and the L-proline is reduced to 6 mM for maintenance.

Callus cultures that reach the "early embryogenic" stage of development are most amenable for starting suspension cultures (Welter et al. 1995). This stage is usually reached in about 12-16 weeks from culture initiation. To generate a suspension culture, approximately 3 g of callus is added to 20 ml of MS medium (Murashige and Skoog, 1962) containing 100 mg/L myo-inositol, 2 mg/L 2,4-D, 2 mg/L 1-naphthaleneacetic acid (NAA), 6 mM L-proline, 200 mg/L casein hydrolysate, 30 g/L sucrose and 5% v/v coconut water (Gibco, Grand Island, N.Y.) added at each subculture. The callus is broken up to suspend the tissue in the medium by pipeting up and down several times with a wide-bore 10 ml pipet. Suspension cultures are maintained in 125 ml Erlenmeyer flasks at 28° C. in the dark on a rotary shaker at 125 rpm. Subculture is performed every 3.5 days by transferring 3 ml of packed cells and 7 ml of old (conditioned) medium to 20 ml of fresh medium. When suspension cultures reach approximately 32-36 weeks in age (from immature embryo callus initiation), they are ready for use in transformation experiments. These cells at this stage could be cryopreserved for future use or could be used in transformation experiments.

Example 2

Initiation of Green Suspension Culture

The non-green suspension cells of Example 1 were used as the starter cells for the establishment of the green suspension cells. Twelve ml packed cell volume (PCV) is transferred to 112 ml of the plastome organizing, non differentiating (PON) medium which is MS medium (Murashige and Skoog, 1962) containing 100 mg/L myo-inositol, 2 mg/L 2,4-D, 2 mg/L 1-naphthalene acetic acid (NAA), 0.5 uM Thidiazuron (TDZ) 6 mM L-proline, 200 mg/L casein hydrolysate, 30 g/L sorbitol, 5 uM Copper sulfate, 1 uM Zinc sulfate at pH 6.0 with 5% v/v coconut water (Gibco, Grand Island, N.Y.) and cultured on an orbital shaker at 180 rpm. A bright intensity of light from cool white fluorescent lamps were provided at a 16/8 hr light and dark cycle at 24-30° C. The cultures turn pink in lower temperatures, which appear to influence the greening of tissue and the morphology of suspension cells.

After 18-24 days of culture initiation and subculturing at 7 day interval to the new medium, the suspension cells start showing green patches and in another week it shows intense over all greening of cells. Until greening of suspensions, the cells do not bulk as much, but once it greens it starts doubling once every 7 days. After 21 days of 3.5 d subculture cycle, the green suspension is subcultured every 7 days and it is maintained in undifferentiated stage. However, the cells become clumpy over a period of 2 months after culture initiation and so it needs to be strained using a tissue sieve to recover the fine suspension that appears to double every 7 days in culture.

Suspension cells 4 weeks after culture initiation in PON medium exhibit a fine and uniform nature of suspension. Cell suspensions exhibit excessive clumpiness after 12 weeks of culture initiation. Straining of the suspension helps restore a fine suspension that doubles on a 7 day subculture. Thirty-six ml PCV when strained yields approximately 6 ml PCV of fine suspension.

Example 3

Light Microscopic and Ultra-structural Investigation of the Initiated Maize Green Suspension Cells Green and non-green suspension cells were squashed between a microscopic slide and cover slip and were observed under a bright-field compound microscope. Aliquots of green suspension cells were used at a stage when the cells were greening ~18 days after transferring the starter cells to the PON liquid medium.

The cells were rather packed together when compared to the non-green suspensions, but they were rather loosely attached and could be readily separable. There were islands of intense green zones distributed on a light green background of cells. On closer observations the cells showed the presence of numerous chloroplasts packed cells, where the chloroplasts are mostly lining the cell wall.

The green and non-green suspension cells were fixed in Karnovsky's fixative and were embedded in epoxy resin (Bryant V. and Watson J. H. L. 1967: A comparison of light microscopy staining methods applied to polyester and three epoxy resins. Henry Ford Hosp. Med. Bull., 15: 65). The thick sections were carried out using glass knives (Hoffman et al. 1983. Polychrome stains for high-resolution light microscopy. Lab Medicine. Vol. 14: 12). For thin sections, staining uranyl acetate was used before the observations under a Hitachi H-600 scope. The median zone of each material was carefully chosen for thin sections after evaluating the integrity of the cells in that zone through thick sections and light microscope observations.

Light microscopic and transmission electron microscopic (TEM) analyses of the chlorophyllous suspension cells show evidence of chloroplasts. TEM examination of non-green suspension also shows loosely arranged cells that are loaded with amyloplasts. Several amyloplasts fuse to form clusters, and such aggregates were the predominant components of the suspension cell cytosol. TEM section of the non-green suspension cells showed amyloplasts, starch, and elaioplasts. A closer view of suspension cells showed a concentration of amyloplasts. The complete absence of chloroplasts was noted in these cells where there were no green plastids with thylakoid membrane system.

The green suspension cells show at least 3 types of plastids, and chloroplast seems to be one of the most predominant plastids observed irrespective of their less green or intense green status of the cells. However, the occurrence of amyloplasts seems to be insignificant compared to the non-green suspensions where it is the most predominant plastid type.

Example 4

Regeneration of Green Suspension

The green suspensions reported here are highly regenerable. They were maintained in the medium for about 2 months. Two-month-old green suspensions need to be strained to isolate the embryo suspensions that are in the differentiating stage. The clumping observed at the older stage appears to be due to the development of embryos. However, the preliminary histological investigation carried out at this stage does not show shoot organization.

The green suspension when plated on regeneration medium germinated normally to produce green plants. After 4-5 weeks on MS medium, the green suspension was regenerated to form plantlets. The plantlets were transferred to the greenhouse, and plants were recovered from them. The regeneration frequency is quite high in the maize regeneration medium.

Example 5

Response of the Green Suspension to the Streptomycin and Spectinomycin

Figure 2:
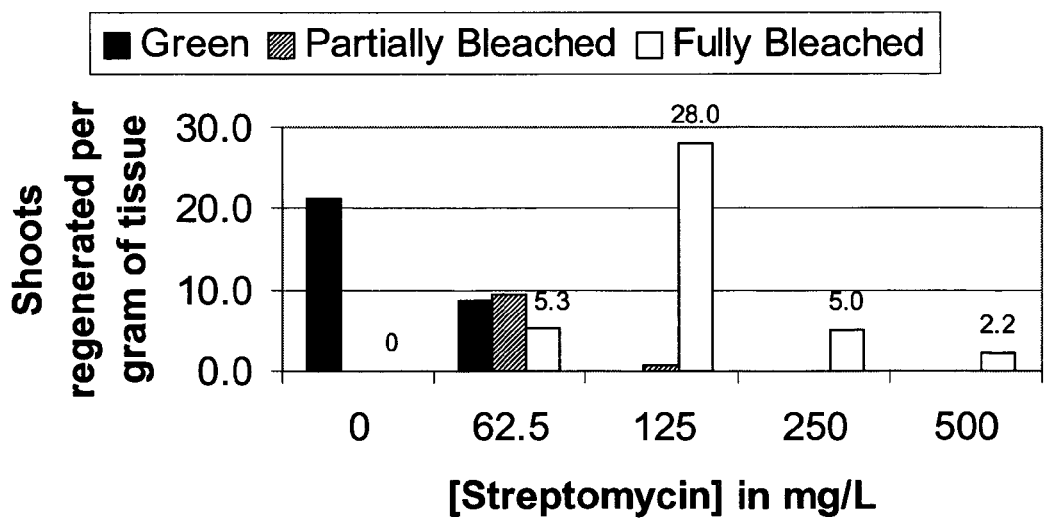
FIG. 2 shows that when germinated in Streptomycin-containing medium, albino plants were recovered at the 125 mg/l concentration. The cells were partially bleached in 250 mg/L Streptomycin. At 500 mg/L there was excessive browning and necrosis indicating that chlorophyll is important for sustenance.

The green suspension did not respond to various spectinomycin concentrations. However, in 500 mg/l Streptomycin after ~4 weeks, growth was inhibited, and the cells were bleached or browned and showed excessive necrosis. When germinated in Streptomycin-containing medium, albino plants were recovered at the 62.5 mg/L concentration (FIG. 2). Most cells were fully bleached in 125 mg/L streptomycin. At 500 mg/L, there was excessive browning and necrosis, which indicates that chlorophyll is important for sustenance of the suspensions.

Example 6

Materials for Plastid Transformation of Maize by Selection for Streptomycin Resistance Plant Material. As the recipient for transformation, maize Hi-II genotype will be used. This genotype has been reported to regenerate readily in culture via type-I, type-II calli and suspension cells (Pareddy et al., 1997; Petolino et al., 2003). These cells are nongreen and contain amyloplasts as the main plastid type. Tnerefore, the use of chloroplast targeted streptomycin or any other similar selection agent does not provide the selection pressure needed to select cells containing chloroplasts with transgenes expressing the enzyme. So, the ideal target tissue for plastid transformation will be the chlorophyllous tissue. However, the unavailability of an efficient green regenerable system similar to tobacco and *Brassica* makes the maize or other cereal plastid transformation difficult. In addition, maize is inherently resistant to spectinomycin, a popular selection agent ubiquitously used in dicot plastid transformation. This narrows the scope of the available selectable marker for this task in maize.

The present invention, the establishment of a regenerable totipotent chlorophyllous suspension, provides an ideal recipient tissue for maize plastid transformation with anticipated selection for the isolation of homoplastomic units for the development of maize transplastomic plants.

Construction of Vector. A plastid transformation was designed according to published reports (Svab and Maliga, 1993; Kavanagh et al., 1999; Assem et al., 2002).

Tissue Culture Media. Maize suspension greening medium (PON) consists of derivatives of the Murashige & Skoog (MS) medium (1962). PON liquid medium: MS salts, Modified MS vitamins, 200 mg/l Casamino Acids (ACH), 100 mg/l myo-Inositol, 2 mg/l 2,4-dichlorophenoxyacetic acid (2,4-D), 2 mg/l naphthaleneacetic acid (NAA), 0.5 uM Thidiazuron (TDZ), 100 mg myo-inositol, 5% v/v coconut water (Gibco, Grand Island, N.Y.), 5 uM Copper sulfate, 1 uM Zinc sulfate, 2.4 mM Proline, and 3% sorbitol, with a pH 6.0.

Shoot induction medium (28, 36-media): This medium contains MS salts, 2.5 mg/l 2,4-D, 5 mg/l benzyladenine (BA) and 3% Sucrose 10 g/l agarose and adjusted to 5.7 pH. 36 medium: MS salts supplemented with 3% Sucrose, 2.5 g/l Gelrite and adjusted to 5.7 pH. The shoots were rooted on SHGA medium. SHGA medium contains SH (Schenk and Hilderbrandt, 1972) salts, myo-inositol, 1 g/l Sucrose, 8 g/l Gelrite® and adjusted to pH 5.8.

Selection media contained 125-500-mg/L streptomycin sulfate. The antibiotics (filter sterilized) were added to media cooled to approximately 50° C. after autoclaving.

Example 7

Transformation and Selection of Streptomycin-Resistant Lines

Nuclear transformation of the Hi-II maize genotype is carried out routinely using Si-Carbide WHISKERS™, and a detailed description of this successful method is recently published (Petolino et al., 2003). Considering the ease at which the suspension cells are readily transformed for nuclear transformation, this methodology can be employed to deliver the plastid vector to the chloroplast of the chlorophyllous suspension cells. The method is described below:

In a chemical fume hood, about 410-420 mg of dry silicon carbide WHISKERS™ (Silar SC-9, Advanced Composite Materials Corp, Greer, S.C.) are transferred to preweighed 30 ml polypropylene centrifuge tubes (Fisher, Pittsburgh, Pa.). Gloves and a respirator are worn while the weighing and transfer is performed, and damp paper towels are spread out so as to immobilize any spilled WHISKERS™ which, when dry, represent a serious respiratory hazard. The centrifuge tubes containing the WHISKERS™ are autoclaved on a slow release cycle and stored at room temperature. Immediately before use, a 5% w/v suspension is made by adding sterile "osmotic medium" (see below) and vortexing at maximum speed for 60 seconds. Suspended WHISKERS are transferred using wide-bore pipettes or pipette tips.

Twenty-four hours prior to WHISKERS treatment 12 ml of settled cell volume and 28 ml of conditioned medium are transferred to PON liquid medium. On the day of WHISKERS treatment, the cells are given an osmotic pretreatment by drawing off the conditioned medium, replacing it with 72 ml of osmotic medium (same medium with the addition of 0.25 M sorbitol and 0.25 M mannitol), and incubating for 25 minutes at 125 rpm. Following the osmotic pretreatment, the contents of 3 flasks are pooled into one sterile 250 ml centrifuge bottle and allowed to settle for 3-5 minutes. Approximately 200 ml of osmotic medium is then drawn off leaving approximately 50 ml of cells and medium at the bottom of the centrifuge bottle. The osmotic medium is saved to a sterile flask to be reused later on during recovery.

Transformation is carried out by adding 8.1 ml of freshly prepared 5% WHISKERS™ to the chlorophyllous suspension along with 170 μg of DNA. The bottle is immediately transferred to a modified paint mixer (Red Devil Equipment Co., Minneapolis, Minn.) in which the paint can clamp assembly has been retrofitted. The bottle is agitated at maximum speed for 10-15 seconds after which the cells are returned to a 1 L recovery flask in which the solution is diluted with the reserved osmotic medium along with 125 ml of fresh PON liquid medium for a final volume of 375 ml. WHISKER™-treated cells are allowed to recover for 2 hours at 125 rpm at 28° C. in the light.

Following recovery, 3-6 ml aliquots of cell suspension culture are evenly dispensed on 5.5 cm No. 4 filter paper discs (Whatman International Ltd., Maidstone, UK) resting on a two -piece Buchner funnel and liquid medium aspirated through a filter flask. The filter paper with cells are then transferred to 60×20 mm Petri dishes containing PON-Agarose semi-solid N6 medium with 2 mg/L 2,4-D, 100 mg/L myo-inositol, 30 g/L sucrose, and 7 g/L Sea Plaque Agarose along with 125 mg/l Streptomycin at pH 6.0. Each bottle will result in 60 filter plates. Plates are then wrapped with gas permeable micropore surgical tape (3M Corporation, St. Paul, Minn.) and incubated at 28° C. under cool white light for selection. Alternately, the streptomycin selection could be carried out in PON liquid medium with 125-500-mg/L streptomycin. The cultures were transferred to fresh antibiotic selection medium on a 7-d cycle until green, red fluorescing (under fluorescent scope) sectors are isolated. At this point, molecular analysis is carried out to evaluate the nature of the gene integration to see if the cells have reached the homoplastomic status. The sectors will be further subjected to selection pressure until homoplastomy and then they are regenerated to recover trans-homo-plastomic plants.

Example 8

Southern Hybridization Analysis of Total Cellular DNA to Verify Plastid Transformation Streptomycin resistance may be due to expression of aminoglycoside adenyltransferase (aadA; an enzyme detoxifying spectinomycin and streptomycin) in plastids (Svab and Maliga, 1993), expression of aadA in the nucleus (Svab et al., 1990), or spontaneous mutation (Fromm et al., 1987; Svab and Maliga, 1991). Southern hybridization can be performed to identify plastid transformants in the streptomycin resistant green cell lines isolated. Total cellular DNA was isolated, and restriction enzyme-digested DNA can be electrophoresed in 0.7% agarose gels and transferred to nylon membrane (Amersham) using the PosiBlot transfer apparatus (Stratagene). Blots can be probed by using Rapid Hybridization Buffer (Amersham) with $^{32}$P labeled probes generated by random priming (Boehringer-Mannheim). It is important to discriminate the nuclear aadA transformation when hybridizing with the targeting ptDNA probe; the Southern blot analysis method needs to be optimized for the high-copy (10,000 per cell) chlorophyllous suspension cells, as a ptDNA signal cannot be detected with a few nuclear aadA copies. Spontaneous mutants have wild-type ptDNA targeting fragment on Southern blots and no PCR-amplifiable aadA gene. It is also important to check the homoplastomy/heteroplastomy status of the green selected sectors (Lössl et al., 2003). Homoplastomy refers to a pure population of plastid genomes, either within a plastid or within a population contained in plant cells and tissues. Homoplastomic plastids, cells, or tissues are genetically stable because they contain only one type of plastid genome. Hence, they remain homoplasmic even after the selection pressure has been removed. Selfed progeny are also homoplastomic. Heteroplastomy refers to the presence of a mixed population of different plastid genomes within a single plastid or in a population of plastids contained in plant cells or tissues.

Example 9

PCR Amplification of Inserted Aminoglycoside Adenyltransferase Sequences

DNA sequences can be amplified according to standard protocols. Streptomycin resistance being the result of aminoglycoside adenyltransferase (aadA) expression may be verified by PCR amplification (Assem et al, 2002) from the isolated green sectors.

Transplastomic Maize plants. The green sectors can be regenerated by passing them through the 28 and 36-media to develop shoots. The shoots are rooted and the plantlets acclimated in the greenhouse before transplanting them to the 5-gallon pots. The transplastomic maize plants are established in the greenhouse, self pollinated, and allowed to set seed after selfing.

Plant Regeneration and Testing of Fertility. The subject invention is an agricultural breakthrough, as the subject invention provides for plastid transformation in maize using chlorophyllous suspension cells, which is also an aspect of the invention. Based on the foregoing, the chimeric aadA gene, for example, could be inserted in the chlorophyllous ptDNA-targeting cassette. This is suitable to recover plastid transformants following the delivery of the DNA in maize. The frequency of the transformation can be compared with tobacco plastids, which yield on average one transformant per bombarded sample (Svab and Maliga, 1993; Zoubenko et al., 1994). The subject regenerable cell suspensions provide numerous target chloroplasts in large numbers and are especially advantageous for maize.

Example 10

Attempts to Initiate Maize Green Regenerable Callus by Emulating the Mexican Grama Grass Model Unlike cultures of dicotyledonous plant tissues, totipotent chlorophyllous monocot cultures were heretofore never achieved, with the only exception being the report on the Mexican blue grama grass (Aguado-Santacruz et al., 2001; *Plant Cell Reports* 20: 131-136). Attempts were made to use Hi-II suspensions to initiate green embryogenic suspension following the procedure described for grama grass in MPC medium. Freshly thawed embryogenic and actively growing (3.5 days doubling time) regenerable lines of Hi-II maize non green suspension cells were transferred to liquid MPC medium. In these experiments, 4×12 ml PCV of the Hi-II suspension cells were used in 80 mL of MPC medium, and the culture was maintained on an orbital shaker at 70 rpm under continuous cool white fluorescent lighting. The objective here was to develop a photosynthetically active suspension culture of maize with the conditions described for grama grass (Aguado-Santacruz et al., 2001). The culture was maintained on 7 day subculture cycles for about 60 days. The cells turned slimy and necrotic, and no green embryogenic tissue differentiation was observed.

Example 11

Production of Chlorophyllous Rice Culture

Mature seeds of *Oryza sativa* L. cv. *Japonica*, Taipai 309, were dehusked and surface sterilized in 70% (v/v) ethanol for 2-5 min followed by a 30-45 min soak in 50% (v/v) commercial bleach containing a few drops of LIQUI-NOX® (Alconox, Inc., White Plains, New York, N.Y.). The seeds were rinsed 3 times in sterile $H_2O$ and placed on filter paper before being transferred to induction medium [N6 macro elements (Chu, 1978, Proc. Symp. Plant Tissue Culture, Peking Press, p 43-56), B5 micro elements and vitamins (Gamborg et al., 1968, Exp. Cell Res. 50: 151-158, 300 mg/L casein hydrolysate, 500 mg/L L-proline, 500 mg/L L-glutamine, 30 g/L sucrose, 2 mg/L 2,4-D, and 2.5 g/L GELRITE, pH 5.8]. The seeds were cultured on induction medium and incubated in the dark at 28° C. for 3 weeks. Afterwards, emerging primary callus induced from the scutellar region of the embryo was transferred to fresh induction medium for further maintenance. Embryogenic callus displaying hard, compact, nodular structures (appearing, and in some cases not appearing, embryo-like) were selected for subculture.

Embryogenic suspension cultures were initiated by transferring 20-25 pieces (~500 mg) of young, embryogenic callus to a 250 mL flask containing 40 mL of AA medium (Muller et al., Mol. Gen. Genet. 161: 67-76) and then agitating on a shaker at 100-130 RPM in the dark at 28° C. The initial culture, which tended to proliferate as compact, non-friable clumps of tissue, was sub-cultured once a week by replacing 20 mL of spent media with fresh AA media After several weeks, the culture was filtered through a 500 m metal screen to remove large clumps, the agitation speed was increased to 150 RPM to break down cell aggregates, and the subculture schedule was reduced (3-4 days) to achieve a finer culture. After a few months, embryogenic suspension cultures exhibiting rapid growth (2-3 day doubling time) and uniform cell cluster size (50-100 cells per cluster) were established.

Initiation of chlorophyllous rice cultures. Twelve ml PCV of this rice suspension culture was transferred to PON_AA medium (Table 1) and 28 ml of spent medium from the maintenance suspension at the stationary phase of culture. The cultures were transferred to orbital shakers at 180 RPM and in a light regime of 100-150-1 um/sq ft under a 16/8 hr light-dark photoperiod.

TABLE 1

Rice Chlorophyllous Initiation Medium/
PON_AA Liquid Medium

| Ingredients: | amt/L |
|---|---|
| AA I Stock* | 100 mL |
| AA II Stock* | 10 mL |
| AA Vitamins* | 10 mL |
| AA Amino Acids (AAAA)* | 10 mL |
| myo-inositol | 100 mg |
| Sorbitol | 20.00 g |
| GA$_3$ (1 mg/ml stock) | 100 μL |
| Kinetin (1 mg/ml stock) phyto | 200 μL |

TABLE 1-continued

Rice Chlorophyllous Initiation Medium/
PON_AA Liquid Medium

| TDZ (0.1 mM) | 5 ml |
|---|---|
| 2,4-D (10 mg/ml stock) | 200 μL |

*Bring to Volume
*pH: 5.8

| Additions AFTER autoclaving: | amt/L | Final Conc. |
|---|---|---|
| Copper Sulfate (CuSo$_4$) 10 mM* | 0.5 ml | 5 μM |
| Zinc Sulfate (ZnSo$_4$) 2 mM* | 0.5 ml | 1 μM |

*Filter sterilize the stock and store it in dark at 4° C.
*AA medium (Muller et al., Mol. Gen. Genet. 161: 67-76)

The suspension was subcultured on a 7 day cycle. After several weeks of subculture in PON_AA medium the cells turned green with uniform chlorophyllous clusters. These green suspensions have a doubling time of 7 days.

Example 12

Further Analysis of Photosynthesis in Green Maize Suspensions

As discussed in Example 2, dispersed cell suspension tended to form aggregates and could be subcultured routinely every 7 days (doubling time) by transferring 12 ml PCV of the cell suspension into 80 ml of fresh PON liquid medium using a 50-ml pipette with 4mm-diameter tips. The cells remained aggregated. When observed under a fluorescent microscope, the green suspension cells showed spotty red fluorescence indicating chlorophyll auto-fluorescence in these tissues. Conversely, the non-green control suspension cells did not show any red fluorescence. This confirms that the chlorophyll is present only in the green suspension cells.

Again, bright field and transmission electron microscope studies revealed the presence of chloroplasts in the green suspension cells. Two types of chloroplasts were apparent; they were morphologically distinct in terms of their sizes. There were large (and fewer) chloroplasts distributed in the dense cytoplasm of the cell. There were also numerous smaller chloroplasts, seemingly connected by the stromuli, adjacent to the cell wall.

Thus, maize chlorophyllous suspension cells of the subject invention exhibited cells that were loosely attached to neighboring cells with relatively thin cell walls. The cells have no or few small vacuoles indicating that they are highly embryogenic. Chloroplasts showed less lamellations including thylakoid granna. The nuclei were prominent and densely stained. There were numerous mitochondria. Some of the chloroplasts adjacent to the cell wall appeared to have the stromule connecting them. Again, two morphologically different chloroplast were observed frequently in these cells.

12.A.—Chlorophyll Estimation

Figure 3:
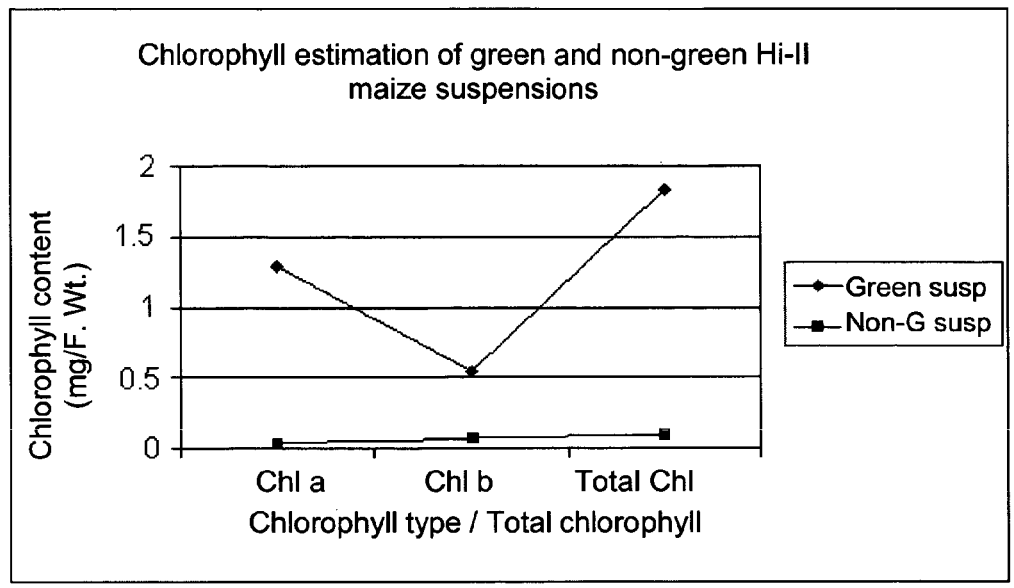
FIG. 3 shows chlorophyll estimation of green and non-green maize suspensions.

Chlorophyll content (total chlorophyll, a and b) of the green suspensions were quantified and compared with the non-green suspension cells. Chlorophyll was extracted from cells with aqueous acetone (80% v/v) from each culture type at the logarithmic phase of the culture stage, and the chlorophyll content was determined using a spectrophotometer (Amon (1949): Plant Physiol 24: 1-15). Chlorophyll a, b, and the total chlorophyll content of the chlorophyllus suspension was much higher than the non green suspension. See FIG. 3.

12.B.—Hill Reaction of Photosynthesis

Artificial electron donors and acceptors are widely used in studies of the electron transfer chain during oxygenic photosynthesis. These compounds are capable of selectively turning on separate parts of the photosynthetic chain. Redox mediators reduced by ascorbate support PS-I dependent reduction of $NADP^+$ or $O_2$ (the Mehler reaction) or methylviologen. Most of the tested electron donors and acceptors are not selective in interactions with components of the electron transfer chain. Redox mediators were first used to evaluate if the cultures carry out Hill reaction. The Hill reaction is demonstrated by measuring oxygen evolution. However, it is more conveniently measured by following the reduction of an artificial electron acceptor to quickly test if the green suspensions are in fact carrying out the process of light reaction. The artificial electron acceptor used to determine the reaction is 2,6-dichlorophenolindophenol (DCIP). The oxidized form of DCIP, but not the reduced form, is blue and absorbs light at 600 nm. In the presence of light the Hill reaction can be measured by the change in A600 of the reaction mixture. The specific reaction is:

$$DCIP^{ox+2} e^- <=> DCIP^{H2red}$$

About 100 mg of green suspension was mixed with 3 ml of DCIP in a spectrophotometer cuvette and was exposed for 90 seconds under light (140 mm s$^{-1}$ m$^{-2}$). These and control non-green suspensions were incubated in dark overnight. The data obtained for both the control (non green suspension) and green suspension were processed according to Hall and Rao ((1994) *Plant Physiology* 102: S139), and the rate of $O_2$ evolution was calculated to be 44.8585 n mol S$^{-1}$ mg Chl$^{-1}$. However, the Hill reaction is more precisely calculated using $O_2$ electrode analysis. Thus, the measurements were also made using the electrode, as reported in the following section.

12.C.—Oxygen Electrode Determination of Photosynthetic Electron Transport.

The oxygen electrode was set up per manufacturer's instructions by covering the silver electrode with layers of KCl solution, cigarette paper, and PTFE gas permeable membrane. The circulating water bath used to maintain a constant temperature of 24° C. during the course of the experiments. An experiment was initiated by the addition of 1 mL of suspension containing 100 mg of the green suspension cells to the electrode chamber. Oxygen uptake within the chamber was limited by the insertion of a plunger to the level of the liquid, and the flea magnet was turned on to assure adequate mixing during each experiment. Data points were collected by LabVIEW 5.1 and sent to an EXCEL spreadsheet. Data points were collected at a rate of 0.2/sec over 70 scans. To determine the rate of respiration, the following assumptions were made: 100% air saturated water=1V=0.287 µmole $O_2$/mL at 18° C.

$$\frac{0.287 \text{ µmol}}{\text{mL}} \times \frac{1000 \text{ nmol}}{\text{µmol}} \times \frac{60 \text{ sec}}{\text{min}} \times \frac{1 \text{ mL}}{1 \text{ V}} \times \frac{\Delta V}{\text{sec}} =$$

$O_2$ consumed in nmol/min

The multiplication factor is thus $$17220 \frac{\text{nmol} \times \text{sec}}{\text{min} \times \text{V}}.$$

Using the $$\frac{\Delta V}{\text{sec}}$$

calculated from the raw data in the EXCEL spreadsheet, the approximate consumption of $O_2$ is calculated by multiplying by 17220 factors shown above.

$O_2$ electrode investigation was carried out to estimate the photosynthetic $O_2$ evaluation in the 100 mg green suspension in 1 ml of the medium. In the presence of light (at 140 mm s$^{-1}$ m$^{-2}$) the amount of $O_2$ evolved was calculated to be 11.35 n mol $O_2$/min. Further experimentation with PSII electron transport inhibitor was carried out to confirm that the $O_2$ evolution was in fact due to photosynthesis.

Photosynthetic electron transport was measured with an oxygen electrode in the absence and presence of diuron (DCMU), a PS-II electron transport inhibitor at several concentrations (Figure below). For each measurement, 100 mg of green and non-green cell suspension was added to the sample cuvette. Temperature of the samples was maintained at 26° C. with a circulating water bath. After a steady rate of respiration was attained, diuron was added under dim light and allowed to absorb for 3 min. A light intensity of 225 µmol M$^{-2}$ S$^{-1}$ photosynthetic photon flux density was used to drive electron transport, and oxygen evolution was measured polarographically.

Whether or not Diuron treatment lead to inhibition of oxygen was investigated using an oxygen electrode. To determine amount of photosynthesis occurring in the cells, respiration rates were measured with and without the exposure of the cells to a strong light source. If the cells are autotrophic, the change in the level of $O_2$ produced as a result of photosynthesis by the light exposed cells should reduce the rate of $O_2$ consumption by the cells as compared to that of the cells in the dark. In addition, diuron, a urea herbicide that inhibits the plant photosystem II, was added to the cells while exposed to light at increasing concentrations in 10 µL increments. The rate of respiration was measured after each addition for approximately 50 sec before any further additions of diuron. The addition of diuron to autotrophic cells while exposed to light should cause an increase in the rate of respiration due to inhibition of photosynthesis. Conversely, non-autotrophic cells should not be affected by the addition of diuron, and respiration would remain unaffected.

For this study, 100 mg tissue of the green suspension was used in combination with several concentrations of diuron. The cultures were kept on an orbital shaker at 26° C. until a sample of 100 mg in 1 mL volume of suspension was transferred to the oxygen electrode. The set up was then illuminated, and the Oxygen evaluation was measured to stabilize conditions of light reaction within the electrode. After about 20 scans, concentrations of diuron were added, and the change in oxygen evolution was recorded. Among the concentrations used, 0.01M had a greater effect of inhibiting the light reaction of photosynthesis. A comparison was made with non-green maize suspensions under the same conditions described here. However, the control treatments did not show any indication of oxygen evolution.

Figure 4:
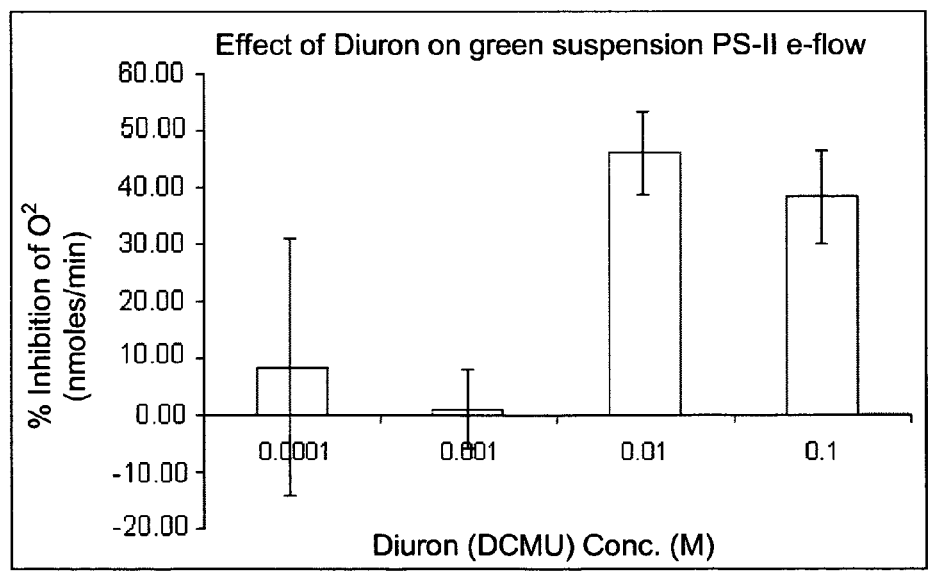
FIG. 4 illustrates the effects of diuron on green suspensions.

Diuron initial dilutions were made in DMSO and control runs were included to determine if the concentration of DMSO added had any inhibitory effect. There was no interference due to the addition of this compound. The inhibition of oxygen was thus attributed solely to the presence of diuron, indicating that the electron transport block cut down the light induced oxygen evolution. See FIG. 4.

12.D.—$^{14}$Carbon Fixation Analysis.

Figure 5:
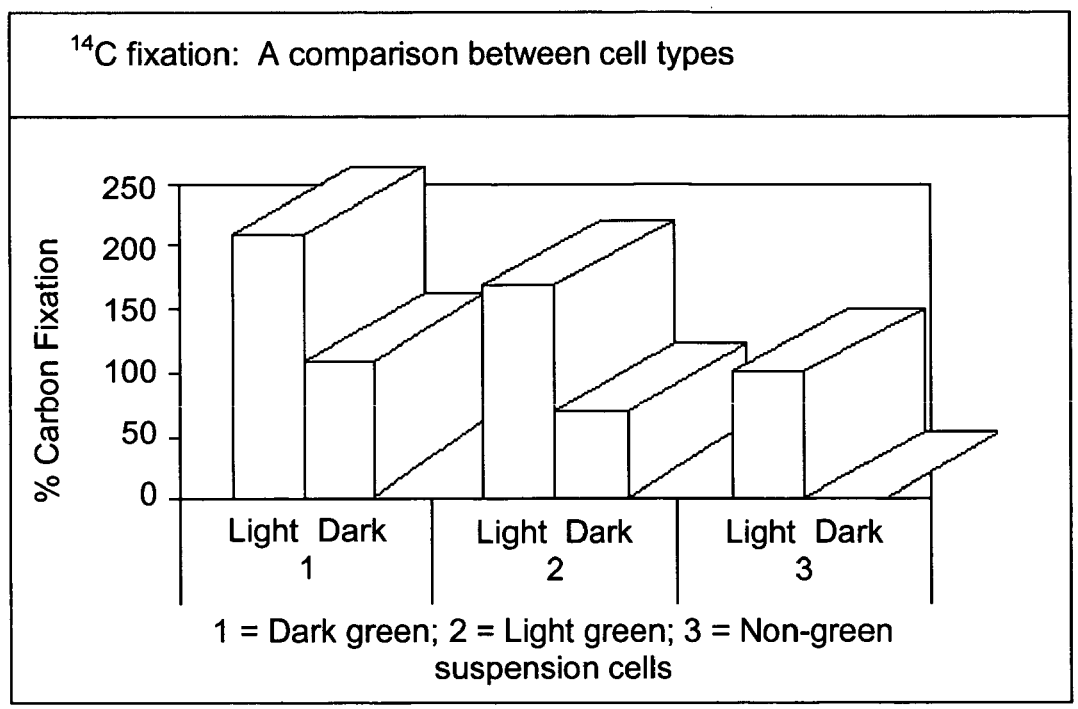
FIG. 5 shows % carbon fixation by dark green, light green, and non-green cells.

To determine if the suspension cells use inorganic carbon source, $^{14}$Carbon fixation analysis was carried out. About 0.5 gm F. Wt of maize Hi-II dark green, light green and non-green suspension cells were tested in light and dark in the presence of NaH$^{14}$CO$_3$. The cells were suspended in 2.5 ml of medium in opaque and transparent vials. Cold NaHCO$_3$ was added to the medium to achieve a final concentration of 5 mM (pH6.8). About 4.66 uCi of NaH$^{14}$CO$_3$ (10.338 ×106 dpm) was added to each of the replicates and incubated on light (100 lum/sq ft) and dark for 1 hr. Cells were then incubated under light with gentle shaking. Cells were collected by centrifuging at 4,500 rpm for 10 min. and washed three times with ice-cold fresh medium. NaOH was added to release unfixed $^{14}$CO$_2$ incubated over night and transferred to a scintillation vial. The washed cells were ground with aqueous scintillation cocktail, and radioactivity (dpm) was measured by liquid scintillation spectroscopy. Uptake of sugars was calculated by subtracting the amount of radioactivity from the control sample. See FIG. 5.

Results were expressed in percent of $^{14}$C uptake per g tissue per h of incubation in light and dark. The light green cells were in the early greening phase of the cells. It is inferred that the $^{14}$C is fixed from the inorganic carbon source and that the cells are autonomous to a certain extent. Similar investigation with $^{14}$C sorbitol can be carried out to confirm that the suspension is capable of utilizing the sole carbon source in the medium, sorbitol.

Example 13

Maize Plastid Transformation Using Micro Aerosol Beaming

Aerosol beam technology employs jet expansion of an inert gas such as helium as it passes from a region of higher gas pressure to a region of lower gas pressure through a small orifice. The expanding gas accelerates aerosol droplets containing the molecules to be introduced into a cell or tissue. The size of the droplet is of particular importance when molecules are to be introduced into small cells or cellular organelles (of less than about 20 microns, for example). The very small aerosol droplets produced by the beam apparatus (U.S. Pat. No. 6,809,232(B1)) are advantageous for plastid transformation of the maize chlorophyllous suspensions that are typically around 1 micron in diameter.

13.A. Target Tissue Preparation.

The target suspensions can be desiccated as mentioned above in the WHISKERS™ Example 7. Then 6 ml aliquots are transferred to each 60×20 mm Petri plate containing PON-Agarose semi-solid medium. The liquid medium is then aspirated, and the target suspension cells are evenly spread on the plate. The target tissues are air dried for 15 minutes in the laminar flow hood with the lids off, and then the tissues are anchored to the plate by floating the desiccated target tissues on melted PON-Agarose N6 medium with 7.0 g/L Sea Plaque® Agarose. Micro aerosol beaming is carried out after the agarose solidifies to anchor the suspension clumps so that the target tissue will remain in place during the process of beaming.

13.B. The Beaming Process.

The chamber vacuum of the beaming unit is maintained at about 30 in. Hg throughout a given run with use of a vacuum pump. The target tissue is placed in the center of an agar plate covering an area of about "a quarter" right below the nozzle tip. The stage movement is controlled by a computer to achieve optimal DNA delivery to the chlorophyllous suspensions. The plastid DNA vector is dissolved 10 mM TE buffer to prepare a 0.2 µg/mL working solution for beaming. The flow rate to the nebulizer is set at 1 ml per hour and each plate sample is beamed by continuously sweeping the aerosol over the target tissue covering "the quarter size" area once within 60 seconds. A total of 60 plates are beamed, and the tissues transferred to light for recovery before applying selection pressure.

13.C. Selection of Maize Transplastomic Sectors and Recovery of Trans-Homo-Plastomic Plants.

Following 0-7 day recovery, the suspension clumps are transferred on to 60×20 mm Petri dishes containing PON-Agarose semi-solid N6 medium along with 125 mg/l Streptomycin at pH 6.0. Plates are then wrapped with gas-permeable micropore surgical tape (3M Corporation, St. Paul, Minn.) and incubated at 28° C. under cool white light for selection. Alternately, the beamed chlorophyllous tissues can be embedded using PON agarose medium with 0.7% Agarose with 125 mg/l Streptomycin. The cultures are kept under light and in antibiotic selection medium until brilliant green, red fluorescing (under fluorescent scope) sectors can be isolated. These green sectors are transferred to fresh cycle of selection. Molecular analysis is carried out to evaluate the nature of the gene integration and the homoplastomic status. The sectors are then further subjected to selection pressure until homoplastomy, and then they are regenerated to recover trans-homoplastomic plants.

REFERENCES

Aguado-Santacruz, G. A., J. L. Cabrera-Ponce, E. Ramirez-Chavez, C. G. Leon-Ramirez, Q. Rascon-Cruz, L. Herrera-Estrella, V. Olalde-Portugal (2001). Establishment, characterization and plant regeneration from highly chlorophyllous embryogenic cell cultures of blue grama grass, *Bouteloua gracilis* (H.B.K.) Lag. ex Steud. Plant Cell Rep 20: 131-136.

Armstrong C, Green C, Phillips R (1991) Development and availability of germplasm with high Type II culture response. Maize Genet Coop News Lett 65: 92-93.

Armstrong, C. L. and Green, C. E. 1985. Establishment and maintenance of friable, embryogenic maize callus and the involvement of L-proline. Planta 164: 207-214

Arnon, D. I. 1949. Copper enzymes in isolated chloroplasts: polyphenol oxidase in *Beta vulgaris*. Plant Physiol. 24: 1-15.

Assem, K., Dhingra, A., and Daniel (2002). Genetic Engineering of Maize Chloroplast Genome. Abs # 888, Poster section 73. Plant Biology 2002, Saturday, August 3-Wednesday Aug. 7, 2002—Denver, Colo., USA.

Borkert C. M., Cox F. R., Tucker M. R., 1998. Zinc and copper toxicity in peanut, soybean, rice and corn in soil mixtures. Commun. Soil Sci. Plant Anal., 29: 2991-3005.

Boynton, J. E., N. W. Gillham, E. H. Harris, J. P. Hosler, and A. M. Johnson. 1988. Chloroplast transformation in Chlamydomonas with high-velocity microprojectiles. Science 240: 1534-1537.

Bryant V. and Watson J. H. L. 1967. A comparison of light microscopy staining methods applied to polyester and three epoxy resins. Henry Ford Hosp. Med. Bull., 15: 65.

Bui V L, Jeanneau M, Do My N T, Vidal J, Tran Thanh Van K (1998) Rapid regeneration of whole plants in Large crabgrass (*Digitaria sanguinalis* L.) using thin cell layer culture. Plant Cell Rep 18: 166-172.

Carrer, H.; Hockenberry, T. N.; Svab, Z.; Maliga, P. (1993). Kanamycin resistance as a selectable marker for plastid transformation in tobacco. MGG,-Mol-gen-genet v. 241(1/2): p. 49-56.

Cho M-J, Jiang W, Lemaux P G (1998). Transformation of recalcitrant barley cultivars through improvement of regenerability and decreased albinism. Plant Sci 138: 229244.

Cho, M. J., C. D. Ha, and P. G. Lemaux, 2000. Production of transgenic tall fescue and red fescue plants by particle bombardment of mature seed-derived highly regenerative tissues. Plant Cell Rep. 19, 1084-1089.

Cho, M. J., H. W. Choi, and P. G. Lemaux, 2001. Transformed T0 orchardgrass (*Dactylis glomerata* L.) plants produced from highly regenerative tissues derived from mature seeds. Plant Cell Rep. 20: 318-324.

Chu C C, Wang C C, Sun C S, Hsu C, Yin K C, Chu C Y, Bi F Y (1975) Establishment of an efficient medium for anther culture of rice through comparative experiments on the nitrogen source. Sci Sinica 18: 659-668.

D'Halluin K, Bonne M, De Beuckeleer M, Leemans J (1992) Transgenic maize plants by tissue electroporation. Plant Cell 4: 1495-1505.

Fromm, H., Edelman, M., Aviv, D. and Galun, E. (1987) The molecular basis of basis of rDNA-dependent spectinomycin resistance in *Nicotiana* chloroplasts. EMBO J., 6, 3233-3237.

Gayoor A, Srivastava P S, Iqbal M. 1999. Morphogenic and biochemical responses of *Bacopa monniera* cultures to zinc toxicity. Plant Science 143: 187-193.

Gordon-Kamm, W. J., T. M. Spencer, M. L. Mangano, T. R. Adams, R. J. Daines, W. G. Start, J. V. O'Brien, S. A. Chambers, W. R. Adams, N. G. Willetts, T. B. Rice, C. J. Mackey, R. W. Krueger, A. P. Kausch, and P. G. Lemaux. 1990. Transformation of maize cells and regeneration of fertile transgenic plants. Plant Cell 2: 603-618

Goulds, T., Maliga, P. & Koop, H. U. (1993) Stable plastid transformation in PEG-teated protoplasts of *Nicotiana tabacum*. Bio/Technology, 11, 95-97

Hall, D. O. & Rao, K. K. (1994) Photosynthesis Studies in Biology (Cambridge University Press). 5th edition. ISBN 0-521-43622-2

Hall, D. O., and Rao, K. K., eds. 1999. Photosynthesis, Sixth Ed. Studies in Biology Series. ISBN 0-521-64257-4 (cloth US$54.95) ISBN 0-521-64497-6 (paper US$19.95) 214 pp. Cambridge University Press (in association with the Institute of Biology), 40 West 20th Street, New York, N.Y. 10011-4211.

Hiei Y, Komari T, Kubo T. (1997). Transformation of rice mediated by *Agrobacterium tumefaciens*. Plant Mol. Biol. 35(1-2): 205-18. Review.

Ishida, Yuji; Saito, Hideaki; Ohta, Shozo; Yukoh, Hiei; Tosihiko, Komari and Takashi, Kumashiro. High efficiency transformation of maize mediated by *Agrobacterium tumefaciens*. Nature Biotechnology, 1996, vol. 14, no. 6, p. 745-750.

Kavanagh T A, Thanh N D, Lao N T, McGrath N, Peter S O, Horváth E M, Dix P J, Medgyesy P (1999) Homeologous plastid DNA transformation in tobacco is mediated by multiple recombination events. Genetics 152: 1111-1122.

Korzeniowska, J., and Stanlslawska-Glublak, E. (2003). Copper Concentration in the top plant tissue as an indicator of Cu toxicity. Electronic Journal of Polish Agricultural Universities, Environmental Development, Volume 6, Issue 1. Available Online: http://www.ejpau.media.pl/series/volume6/issue1/environment/art-02.html.

Koziel, M. G., G. L. Beland, C. Bowman, N. B. Carozzi, R. Crenshaw, L. Crossland, J. Dawson, N. Desai, M. Hill, S. Kadwell, K. Launis, K. Lewis, D. Maddox, K. McPherson, M. R. Meghji, E. Merlin, R. Rhodes, G. W. Warren, M. Wright, and S. V. Evola. 1993. Field performance of elite transgenic maize plants expressing an insecticidal protein derived from *Bacillus thuringiensis*. Biotechnology 11: 194-200.

Laursen, C. M., Krzyzek, R. A., Flick, C. E. et al., Production of fertile transgenic maize by electroporation of suspension culture cells, Plant Mol. Biol., 1994, 24: 51.

Lössl, A., Eibl, C., Harloff, H., Jung, C. and Koop, H. U., (2003): Polyester in transplastomic tobacco: Significant contents of polyhydroxybutyrate are associated with growth reduction. Plant Cell Rep. 21: 891-899.

Lowe, K., B. Bowen, G. Hoerster, M. Ross, D. Bond, D. Pierce and K. B. Gordon 1995. Germline transformation of maize following manipulation of chimeric shoot meristems. Bio Technology New York. 13(7): 677-682

Maliga, P. (1993) Towards pliastid transformation in flowering plants. Trends Biotechnol., 11, 101-106.

McBride K, Schaaf D, Daley M, Stalker D. 1994. Controlled expression of plastid transgenes in plants based on a nuclear DNA-encoded and plastid-targeted T7 RNA polymerase. Proceedings of the National Academy of Sciences, USA 91, 7301-7305.

Muller, A. J. and R. Grafe, 1978. Isolation and characterization of cell lines of *Nicotiana tabacum* lacking nitrate reductase. Mol. Gen. Genet. 161: 67-76.

Murashige T, Skoog F (1962) A revised medium for rapid growth and bioassays with tobacco tissue cultures. Physiol Plant 15: 473-497.

Nanda Kumar PBA, Dushenkov V, Motto H, Raskin I. 1995. Phytoextraction: the use of plants to remove heavy metals from soils. Environmental Science Technology 29: 1232-1238.

Omirulleh, S., M. 'Abrah'am, M. Golovkin., I. Stefanov, M. Karabaev, L. Must'ardy, S. M'orocz, and D. Dudits. 1993. Activity of a chimeric promoter with the doubled CaMV $^{35}$S enhancer element in protoplast-derived cells and transgenic plants in maize. Plant Mol. Biol. 21: 415-428

O'Neill, C, Horvath, G. V., Horvath, E., Dix, P. J. and Medgyesy, P. (1993) Chloroplast transformation in plants: polyethylene glycol (PEG) treatment of protoplasts is an alternative to biolistic delivery systems. Plant J., 3, 729-738.

Palmer JD (1991) Plastid chromosomes: structure and evolution. In: Bogorad L and Vasil IK (eds) The Molecular Biology of Plastids, pp 5-53. Academic Press, San Diego, Calif. Pareddy D, Petolino J, Skokut T, Hopkins N, Miller M, Welter M, Smith K, Clayton D, Pescitelli S, Gould A (1997) Maize transformation via helium blasting. Maydica 42: 143-154

Petolino, J. F., M. Welter, and C. Qihua (2003). WHISKERS—mediated Transformation in Maize. Molecular Methods of Plant Analysis. Pp 147-158. Vol 23 Genetic analysis of Plants. Springer-Verlag. Berlin, Hedelberg.

Ralph PJ, Burchett MD. 1998. Photosynthetic response of *Halophila ovalis* to heavy metal stress. Environmental Pollution 103: 91-101.

Rhodes CA, Pierce DA, Mettler IJ, Mascarenhas D, Detmer JJ. 1989. Genetically transformed maize plants from protoplasts. Science 240, 204-207.

Sambrook et al., *DNA Cloning, A Laboratory Manual*, Cold Spring Harbor Laboratory, 1989 or Ausubel et al. eds. in *Current Protocols in Molecular Biology*, John Wiley and Sons, 1995.

Schenk, R. U. and Hildebrandt, A. C., 1972. "Medium and Techniques for Induction and Growth of Monocotyledonous and Dictoyledonous Plant Cell Cultures." Can. J. Bot. 50: 199-204.

Sikdar, S. R., Serino, G., Chaudhuri, S., and Maliga, P. (1998) Plastid transformation in *Arabidopsis thaliana*. Plant Cell Reports 18: 20-24.

Staub, J. & Maliga, P. (1992) Long regions of homologous DNA are incorporated into the tobacco plastid genome by transformation. Plant Cell 4, 39-45.

Svab, Z. and Maliga, P. (1991) Mutation proximal to the tRNA binding region of the *Nicotiana* plastid 16S rRNA confers resistance to spectinomycin. Molec. Gen. Genet. 228, 316-319

Svab, Z. and Maliga, P. (1993) High-frequency plastid transformation in tobacco by selection for a chimeric aadA gene. Proc. Natl. Acad. Sci. USA, 90, 913-917.

Svab, Z., Hajdukiewicz, P. and Maliga, P. (1990) Stable transformation of plastids in higher plants. Proc. Natl. Acad. Sci. USA, 87, 8526-8530.

Svab, Z., Harper, E. C., Jones, J. D. G. and Maliga, P. (1990) Aminoglycoside-3"-adenyltransferase confers resistance to spectinomycin and streptomycin in *Nicotiana tabacum*. Plant Mol. Biol. 14, 197-205.

Taiz L, Zeiger E. 1998. Mineral nutrition. In: Taiz L, Zeiger E, eds. Plant physiology, 2nd edn. Sunderland, Mass., USA: Sinauer Associates, Inc, Publishers, 103-124.

U.S. Pat. No. 2,001,0031496A1. Compositions and methods for plant transformation and regeneration. 21 pages.

U.S. Pat. No. 5,302,523. Transformation of plant cells. 5 pages.

U.S. Pat. No. 5,451,513. Method for stably transforming plastids of multicellular plants. 21 pages.

U.S. Pat. No. 5,545,817. Enhanced expression in a plant plastid. 10 pages.

U.S. Pat. No. 5,545,818(A,X6). Expression of *Bacillus thuringiensis* cry proteins in plant plastids. 11(10, 1) pages.

U.S. Pat. No. 5,576,198. Controlled expression of transgenic constructs in plant plastids. 15 pages.

U.S. Pat. No. 5,736,369. Method for producing transgenic cereal plants. 16 pages.

U.S. Pat. No. 5,932,479. Genetic engineering of plant chloroplasts. 12 pages.

U.S. Pat. No. 6,140,555. Methods for maize transformation coupled with adventitious regeneration utilizing nodal section explants and mature zygotic embryos. 24 pages.

U.S. Pat. No. 6,235,529(B1). Compositions and methods for plant transformation and regeneration. 19 pages.

U.S. Pat. No. 6,486,384(B1). Methods and compositions for transformation of cereals using cultured shoot meristematic tissue. 21 pages.

U.S. Pat. No. 6,515,206(B1). Plastid transformation of *Brassica*. 29 pages.

USEPA, 1992. Technical support document for land application of sewage sludge. Document no. EPA-822/R-93-OO1a. USEPA Office of water, Washington, D.C.

Welch R M. 1995. Micronutrient nutrition of plants. Critical Reviews in Plant Sciences 14: 49-82

Welter ME, Clayton DS, Miller MA, Petolino JF (1995) Morphotypes of friable embryogenic maize callus. Plant Cell Rep 14: 725-729.

WO Patent No.: 95/16783(A1). Controlled expression of transgenic constructs in plant plastids. 48 pages.

WO Patent No.: 97/32977(A1). Plastid Transformation in *Arabidopsis*. 46 pages.

Zhang S, Cho M-J, Koprek T, Yun R, Bregitzer P, Lemaux PG (1999). Genetic transformation of commercial cultivars of oat (*Avena sativa* L.) and barley (*Hordeum vulgare* L.) using in vitro shoot meristematic cultures derived from germinated seedlings. Plant Cell Rep 18: 959-966.

Zhang S, Cho M-J, Koprek T, Yun R, Bregitzer P, Lemaux PG (1999). High-frequency transformation of oat via microprojectile bombardment of seed-derived highly regenerative cultures. Plant Cell Rep 18: 959-966.

Zhao, Z et al. 1998. Molecular analysis of T0 plants transformed by *Agrobacterium* and comparison of *Agrobacterium*-mediated transformation with bombardment transformation in maize. MNL 72: 34-37

Zoubenko, O. V., Allison, L. A., Svab, Z. and Maliga, P. (1994) Efficient targeting of foreign genes into the tobacco plastid genome. Nucleic Acids Res., 22, 3819-3824.

The invention claimed is:

1. A culture of chlorophyllous totipotent maize cells, wherein said cells are photoautotrophic, wherein said cells have functional chloroplasts when grown in a sugar-free medium comprising thidiazuron, copper, zinc, and sorbitol.

* * * * *